US008492412B2

(12) United States Patent
Magaña Castro et al.

(10) Patent No.: US 8,492,412 B2
(45) Date of Patent: Jul. 23, 2013

(54) GEL CONTAINING PIRFENIDONE

(75) Inventors: José Agustín Rogelio Magaña Castro, Mexico City (MX); Laura Vázquez Cervantes, Mexico City (MX); Juan Socorro Armendáriz Borunda, Mexico City (MX)

(73) Assignee: Cell Therapy and Technology, S.A. De C.V., Mexico City (MX)

( * ) Notice: Subject to any disclaimer, the term of this patent is extended or adjusted under 35 U.S.C. 154(b) by 328 days.

(21) Appl. No.: 12/673,304

(22) PCT Filed: Aug. 14, 2008

(86) PCT No.: PCT/MX2008/000107
§ 371 (c)(1),
(2), (4) Date: Apr. 28, 2010

(87) PCT Pub. No.: WO2009/022899
PCT Pub. Date: Feb. 19, 2009

(65) Prior Publication Data
US 2011/0224265 A1    Sep. 15, 2011

(30) Foreign Application Priority Data

Aug. 14, 2007    (MX) .................. MX/A/2007/009796

(51) Int. Cl.
*A01N 43/40*    (2006.01)
*A61K 31/44*    (2006.01)

(52) U.S. Cl.
USPC ........................... 514/350; 514/345; 514/354

(58) Field of Classification Search
USPC .................................................. 514/350, 345
See application file for complete search history.

(56) References Cited

U.S. PATENT DOCUMENTS

| 4,376,118 | A | * | 3/1983 | Daher et al. .................. 514/153 |
| 5,811,130 | A | * | 9/1998 | Boettner et al. .............. 424/643 |
| 5,958,420 | A | * | 9/1999 | Jenson ........................ 424/771 |
| 6,365,131 | B1 | * | 4/2002 | Doshi et al. .................... 424/49 |
| 2004/0029946 | A1 | * | 2/2004 | Arora et al. .................... 514/406 |

FOREIGN PATENT DOCUMENTS

| WO | 00/16775 A1 | 3/2000 |
| WO | 2004/073713 A1 | 9/2004 |

OTHER PUBLICATIONS

International Search Report for Application No. PCT/MX2008/000107, dated Dec. 9, 2008.

* cited by examiner

*Primary Examiner* — Sreeni Padmanabhan
*Assistant Examiner* — Layla Soroush
(74) *Attorney, Agent, or Firm* — Nelson Mullins Riley & Scarborough LLP; Jill Gorny Sloper, Esq.; Jeanne M. DiGiorgio

(57) ABSTRACT

The invention relates to a gel composition containing pirfenidone, which is advantageous over other cutaneously administered pharmaceutical forms known in the prior art and which can be used in treatment for the restoration of tissues with fibrotic lesions and for the prevention of fibrotic lesions.

5 Claims, No Drawings

GEL CONTAINING PIRFENIDONE

FIELD OF INVENTION

The present invention is related to a gel formula that contains Pirfenidone, which offers advantages over other pharmaceutical forms of known cutaneous administration in the state of the technique.

BACKGROUND OF THE INVENTION

The 5-methyl-1-phenyl-2(1H)-pyridone, formula;

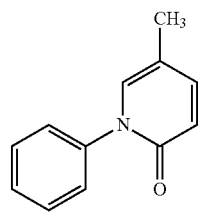

It is a drug that has been applied in the restoration of tissues with lesions with fibrosis and the prevention of fibrotic lesions. This compound, Pirfenidone, it is by itself a known compound and its pharmacological effects has been described, for example, in Japanese applications numbers 87677/1974 and 1284338/1976, as an anti-inflammatory agent that includes antipyretic and analgesics. The U.S. Pat. Nos. 3,839,346, published Oct. 1, 1974; the U.S. Pat. No. 3,974,281, published Aug. 10, 1976; the U.S. Pat. No. 4,042, 699 published Aug. 16, 1977, and the U.S. Pat. No. 4,052,509 published Oct. 4, 1977, which described the methods for the obtained Pirfenidone, as well as its use as an anti-inflammatory agent. In the Mexican patent 182, 266 the antifibrotic activity of the 5-methyl-1-phenyl-2(1H)-pyridone is described.

Different resources and treatments have been used to the date and none of them have shown to be really effective. Pirfenidone has shown its efficacy as an anti-fibrotic agent in different pathologies and organs, and has been demonstrated in previous works, where we have observed an effect on the fibroblasts and the production of collagen and extracellular matrix, as well as in experimental models and in clinical tests also.

Many substances could form gels when a gelificant agent is added. This is use in many diverse products in the manufacturing industry, from food to paint, passing through adhesives.

Gels are also important in the chemistry part related with the processes SOL_GEL and in the synthesis of solid materials with nanopores.

Gels are classified in: aqueous (hydrogels) or organic (organogels), dependingo if the aqueous component is water or an organic solvent; organic or inorganic in nature, colloidal or thick grain, according to the size of the particles; and rigid gels, elastic or tixothrophic, according to its mechanic properties.

The hydrocolloids are substances that are produced from vegetable and animal proteins or multiple sugars. They have the capacity to swell themselves and to bind to water. The hydrocolloids are used to thicken, solidify and stabilize food.

OBJECT OF THE INVENTION

The object of the present invention is to provide a gel composition for its cutaneous administration that contains Pirfenidone, a viscous agent; a solubilizer; a non ionic solubilizer; a conserving agent; a neutralizer agent and purified water.

Also, it is the object of the present invention to provide a process of manufacture of a gel that contains pirfenidone for its cutaneous application.

Another objective of the present invention is to provide a gel medicine to be used as an anti-fibrotic and anti-inflammatory agent.

SPECIFICATION OF THE INVENTION

Composition of the Gel

The composition of the gel contains from 2 to 12% of Pirfenidone is elaborated utilizing from 0.4 to 1.2% of a viscous agent, from 10 to 30% of a solubilizer, from 5 to 15% of a non ionic solubilizer, from 0.2 to 1% of a conserving agent, from 0.4 to 1.2% a neutralizer agent and the rest of purified water. The viscous agent is selected from a carbomer 940 (MR); Carbomer Homopolymer Type A, cellulose derivatives; gums; poloxamers, ethyl alcohol and propylene glycol; the conserving agent is selected from a group consisting of Diazolidinyl urea, iodopropynyl butylcarbamate; methylparaben and a mix of these compounds; the neutralizer agent is selected from a group of primary, secondary and tertiary aliphatic amines of the mono-, bi- and triethanolamine type, and of the hydroxide alkaline metals, such as sodium hydroxide.

An example of the composition of the gel is shown in the table 1:

| Component | Quantity (g) | % |
|---|---|---|
| Pirfenidone | 8 | 8 |
| Viscous agent | 0.5 | 0.5 |
| Solubilizer | 20 | 20 |
| Non ionic solubilizer | 11.5 | 11.5 |
| Conserving agent | 0.5 | 0.5 |
| Neutralizer | 0.5 | 0.5 |
| Purified water up to | 100 | 59 |

The gel containing Pirfenidone is manufactured as follows:
a) Mix 50% of the total water to be used with the viscous agent, allowing the complete humectation of the viscous agent;
b) Mix separately and with constant agitation the Pirfenidone with the solubilizer agent;
c) Dissolve separately the non ionic solubilizer agent in the 25% water to be used at 40° C., once dissolved, the 15% of the total water is added;
d) Add the solution from part c) to the mix from part b), agitate until the mix is homogenate.
e) Dilute the neutralizer agent in 10% of the total water to use, agitate until the mix is homogenate; and
f) Add with constant agitation and homogenate in each addition to the mix from part a) the solution from part d); the conservative and the solution from part e).

A prepared composition according to procedure describe is shown in table 2.

| Component | Quantity (g) |
|---|---|
| Pirfenidone | 8 |
| Carbomer | 0.5 |

-continued

| Component | Quantity (g) |
|---|---|
| N-methylpirrolidone | 20 |
| Macrogolglycerol Hidroxiestearate 40 | 11.5 |
| Diazolidinilurea and Iodopropinil-butilcarbamate | 0.5 |
| Triethanoalamine | 0.5 |
| Purified water up to | 100 |

These compositions are shown in an example mode, but they are not limited in any level of the reach of the description of the present invention.

The invention claimed is:

1. A composition of Pirfenidone gel consisting of 8% Pirfenidone, 0.5% of a viscous agent, 20% of a solubilizer, 11.5% of a non ionic solubilizer, 0.5% of a conserving agent, 0.5% of a neutralizer agent and 59% of purified water.

2. The composition of claim 1, wherein
   (a) the viscous agent is selected from the group consisting of a Carbomer 940 (MR), Carbomer Homopolymer Type A, a cellulose derivative, a gum, and a poloxamer;
   (b) the solubilizer is selected from the group consisting of N-methylpyrrolidone, ethyl alcohol, and propylene glycol;
   (c) the conserving agent is selected from the group consisting of diazolidinyl urea, iodopropynyl butylcarbamate, methylparaben, propylparaben, and mixes of these conserving agents;
   (d) the neutralizer agent is selected from the group consisting of primary, secondary and tertiary aliphatic amines of the mono-, bi-, and triethanolamine type, and a hydroxide alkaline metal.

3. The composition of claim 2, wherein the viscous agent is Carbomer 940 (MR), the solubilizer is N-methylpyrrolidone, the conserving agent is diazolidinyl urea, and the neutralizer agent is triethanolamine.

4. The composition of claim 2, wherein the hydroxide alkaline metal is sodium hydroxide.

5. The composition of claim 2, wherein the viscous agent is Carbomer 940 (MR), the solubilizer is N-methylpyrrolidone, the conserving agent is iodopropynyl butylcarbamate, and the neutralizer agent is triethanolamine.

* * * * *

UNITED STATES PATENT AND TRADEMARK OFFICE
CERTIFICATE OF CORRECTION

| | | |
|---|---|---|
| PATENT NO. | : 8,492,412 B2 | Page 1 of 1 |
| APPLICATION NO. | : 12/673304 | |
| DATED | : July 23, 2013 | |
| INVENTOR(S) | : Castro et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 401 days.

Signed and Sealed this
Eighth Day of October, 2013

Teresa Stanek Rea
*Deputy Director of the United States Patent and Trademark Office*